United States Patent [19]

Patrick et al.

[11] Patent Number: 5,251,765

[45] Date of Patent: Oct. 12, 1993

[54] APPARATUS AND METHOD FOR SEGREGATING RODS OF UNDESIRABLE ALLOY COMPOSITION

[75] Inventors: Stanley S. Patrick, Columbia, S.C.; Robert E. Shannon, Penn Township, Westmoreland County, Pa.

[73] Assignee: Westinghouse Electric Corp., Pittsburgh, Pa.

[21] Appl. No.: 611,609

[22] Filed: Nov. 13, 1990

[51] Int. Cl.$^5$ .................. B07C 5/344; G01N 27/14
[52] U.S. Cl. ................................ 209/520; 209/546;
209/571; 209/600; 209/916; 209/934; 324/451
[58] Field of Search ............... 209/509, 517, 518, 520,
209/546, 552, 556, 570, 571, 600, 606, 916, 921,
934, 942; 324/451; 136/202; 376/245, 247, 257, 261

[56] References Cited

U.S. PATENT DOCUMENTS

| | | | |
|---|---|---|---|
| 2,907,458 | 10/1959 | Scharein | 209/520 |
| 3,263,809 | 8/1966 | Mandula, Jr. et al. | 209/570 X |
| 3,667,032 | 5/1972 | Summers | 324/451 |
| 3,787,761 | 1/1974 | Grossman et al. | 376/257 X |
| 4,019,364 | 4/1977 | Maddox | 324/451 X |
| 4,134,064 | 1/1979 | Jacobs et al. | 376/257 X |
| 4,156,840 | 5/1979 | Rowsey et al. | 324/451 |
| 4,243,939 | 1/1981 | Grossman et al. | |
| 4,320,344 | 3/1982 | Nicholas | 324/451 |
| 4,347,622 | 8/1982 | Bernatowicz et al. | 376/257 X |
| 4,542,345 | 9/1985 | Tomasulo | 324/451 |
| 4,564,498 | 1/1986 | Grossman et al. | 376/245 |
| 4,673,877 | 6/1987 | Sakamoto et al. | 376/245 X |
| 4,822,552 | 4/1989 | Ahmed et al. | 376/257 |

FOREIGN PATENT DOCUMENTS

| | | | |
|---|---|---|---|
| 0224554 | 11/1962 | Austria | 209/517 |
| 0280925 | 9/1988 | European Pat. Off. | 376/257 |
| 1056857 | 5/1959 | Fed. Rep. of Germany | 209/517 |
| 0133583 | 1/1979 | Fed. Rep. of Germany | 324/451 |
| 0529401 | 6/1977 | U.S.S.R. | 324/451 |
| 1117088 | 10/1984 | U.S.S.R. | 209/556 |

OTHER PUBLICATIONS

Patent Associated Literature A135-7513'Q; *Applied Physics Letters,* vol. 26, No. 12, pp. 675-677, Jun. 15, 1975; "Distribution of charge in electrets".
Patent Associated Literature J045-7605-X; *Journal of Physics E,* vol. 9, No. 6, pp. 435-437, Jun. 1976; "Continuous and rapid measurement of Seebeck coefficient using operational amplifier circuitry".
Patent Associated Literature S58240023; *Chemical Instrumentation,* 6(2), 133-141 (1975); "A Dynamic Seebeck Coefficient Measuring Device For High Resistivity Materials".

*Primary Examiner*—Michael S. Huppert
*Assistant Examiner*—Edward M. Wacyra

[57] ABSTRACT

Apparatus and method for segregating elongate cylindrical rods of undesirable alloy composition from rods having a desired alloy composition is disclosed. The apparatus includes a rod segregation table having an upper rod transport side for individually moving rods transversely in substantially parallel spaced relation across the table. A thermoelectric tester is positioned at an intermediate rod test position under the upper rod transport side of the table and includes two spaced electrodes maintained at different temperatures and being adapted and arranged to engage a rod as it is moved into the rod test position. A signal representative of the thermoelectrically induced voltage in the rod between the electrodes is generated and compared to a predetermined value. An offset drive signal is generated when the signal representative of the induced thermoelectric voltage is different from the predetermined value. A rod offset drive mechanism positioned on the table receives the offset drive signal and advances a rod longitudinally to an offset position on the table.

16 Claims, 7 Drawing Sheets

APPARATUS AND METHOD FOR SEGREGATING RODS OF UNDESIRABLE ALLOY COMPOSITION

FIELD OF THE INVENTION

This invention relates to an apparatus and method for segregating elongate cylindrical rods of undesirable alloy composition from rods having a desired alloy composition.

BACKGROUND OF THE INVENTION

Nuclear fuel rods often are produced from alloys of zirconium metal. Zirconium provides a combination of high corrosion resistance, high strength at moderate and high temperatures, and a low neutron-absorption cross section which makes the metal ideal as a fuel rod cladding material.

However, slight impurities in zirconium adversely affect the mechanical properties of the metal, especially at higher temperatures such as the operating temperature of a nuclear fuel reactor. As a result, special zirconium alloys, such as zircaloy and zirlo, have been developed for greatly improving the oxidation resistance of the fuel rod at higher temperatures. As a result, nuclear fuel manufacturers are providing nuclear fuel rods made of zirlo and zircaloy cladding to resist corrosion and degradation at higher temperatures.

In some nuclear reactor cores, zirlo alloy fuel rods are more preferred because the special alloy materials found in the zirlo makes that material more corrosion resistant than zircaloy. It has been determined that zircaloy rods may fail if they inadvertently are inserted in a reactor core designed for use with zirlo rods. This may cause a reactor to shut down resulting in increased costs and maintenance.

In some nuclear fuel manufacturing plants, zircaloy and zirlo fuel rods are processed concurrently with each other. It is possible during the manufacturing process for one type of rod, such as a zircaloy rod, to become mixed into a group of zirlo rods. Because both zirlo and zircaloy rods are similar in appearance, weight, dimension and handling characteristics, it is almost impossible to segregate the zirlo and zircaloy fuel rods without appropriate inspection procedures. It is necessary, therefore, to segregate zirlo and zircaloy fuel rods during processing.

Additionally, any inspection and segregation process for the rods must be nondestructive to the rods. Manufacturing nuclear fuel rods is an expensive process and any destructive alloy verification and segregation system is unacceptable and costly. Statistical random selection of fuel rods for alloy verification and segregation also is unacceptable because statistical inspection procedures cannot give one hundred percent verification of each processed fuel rod. Additionally, any inspection and segregation process should be automated with appropriate rod and material handling systems to accommodate peak production requirements and facilitate the segregation of different fuel rods.

It has been determined that a thermoelectric testing system, commonly referred to as a Seebeck effect testing system, is more desirable than other non-destructive testing methods such as x-ray fluorescence which requires expensive equipment, or eddy current testing which requires a separate test coil. An eddy current testing system is considered impractical in a nuclear fuel rod production environment because different rods of varying diameters often are processed together. The eddy current test coil is sized depending on the dimensions of a rod or other material to be tested. Thus, an eddy current testing apparatus may not only require a number of different sized test coils, but also the means for measuring the rods and transferring the rods to the appropriate coil.

SUMMARY OF THE INVENTION

The apparatus and method of the present invention segregates elongate cylindrical rods of undesirable alloy composition from rods having a desired alloy composition. The apparatus includes a rod segregation table having an upper rod transport side and defining a rod entry side and a rod discharge side. Rod movement means individually moves rods transversely in spaced relation across the rod segregation table from the rod entry side to an intermediate rod test position, and to the rod discharge side.

Thermoelectric test means is positioned at the rod test position and includes at least two spaced electrodes maintained at different temperatures. The electrodes are adapted and arranged to engage a cylindrical rod to be tested as it is moved into the rod test position. Means connected to the thermoelectric means compares signals representative of the induced thermoelectric voltage to a predetermined value. When the signal representative of the induced thermoelectric voltage is different from the predetermined value, an offset drive signal is generated. Rod offset drive means positioned on the rod segregation table at the rod test position receives the offset drive signal. The rod offset drive means advances the rod longitudinally to an offset-position on the rod segregation table from the longitudinal position of other rods moved along the rod segregation table.

The thermoelectric test means includes an electrode support fixture supported by the rod segregation table. The electrode support fixture includes a housing positioned under the table. Housing support means is fixed to the table and supports the housing for movement of the housing from a first rod testing position to a second, laterally offset non-testing position. The spaced electrodes are supported by the housing and are positioned to engage the bottom portion of a rod when the housing is positioned in the rod test position.

Rod engaging clamp means is carried by the housing and is vertically moveable between 1) a lower position where the rod engaging clamp means is positioned beneath the upper rod transport side of the table, 2) a raised position above the level of said upper rod transport side and 3) an intermediate position where the rod engaging clamp means is engaged with the upper surface of a rod positioned in the rod test position. The rod engaging clamp means includes an air cylinder mounted on the housing and having a downwardly extending output shaft. A cross member is mounted on the air cylinder output shaft and includes two substantially parallel, spaced and vertically extending shafts having lower ends mounted to the cross member. An elongate rod clamp member extends between the upper ends of each shaft and is mounted thereto. The elongate rod clamp member includes a lower rod engaging surface for engaging the upper surface of a rod positioned in the rod test position.

BRIEF DESCRIPTION OF THE DRAWINGS

Some of the objects and advantages of the present invention having been stated, other will appear as the description proceeds, when taken in conjunction with the accompanying drawings, in which.

DETAILED DESCRIPTION OF THE PREFERRED EMBODIMENT

Figure 1:
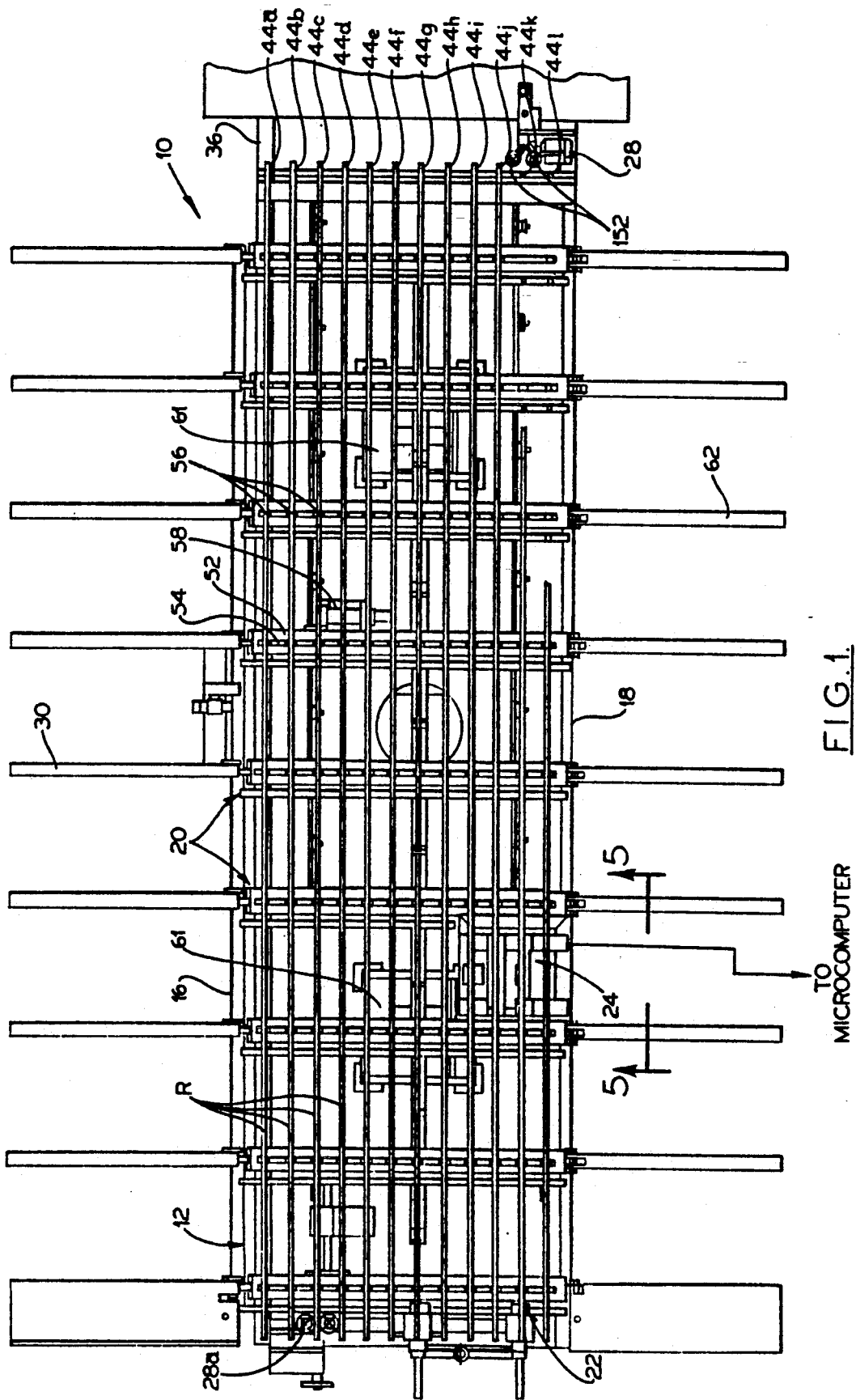
FIG. 1 is a plan view of the rod segregation table.

Referring now to FIG. 1, there is shown a plan view of the apparatus, indicated generally at 10, in accordance with the present invention which segregates elongate cylindrical rods of undesirable alloy composition from rods having a desired alloy composition. The apparatus 10 can be used with any number and type of cylindrical rods of varying compositions for segregating those of undesirable alloy composition from those of desired alloy composition. However, for purposes of the present description, the apparatus lo will be described with reference to the processing of nuclear fuel rods of two different zirconium alloys, i.e., the desired zirlo and other zircaloy fuel rods.

Figure 5:
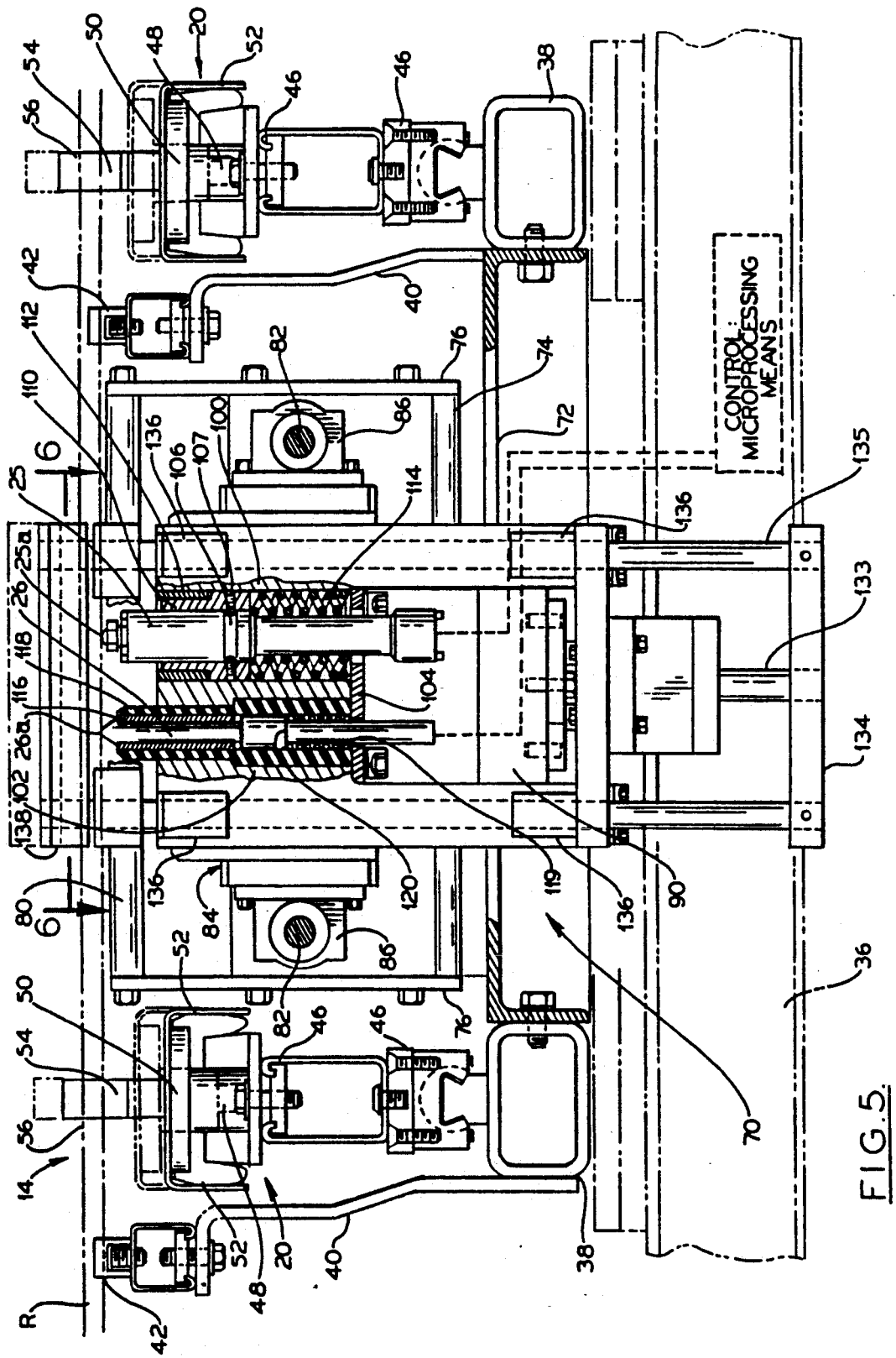
FIG. 5 is a partial side sectional view of the frame, the thermoelectric test housing and the electrodes supported by the housing.
Figure 6:
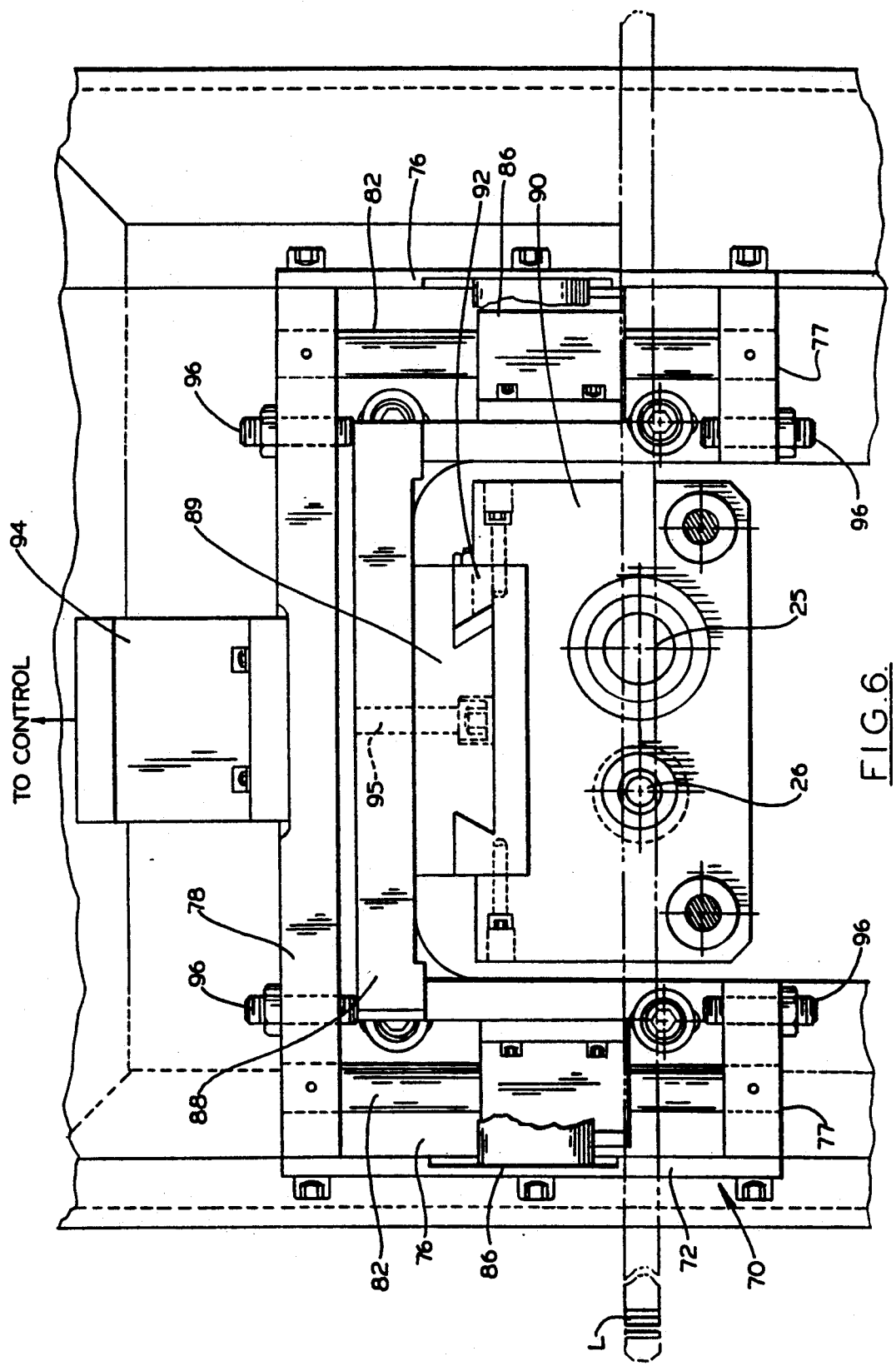
FIG. 6 is a partial sectional view taken along line 6—6 of FIG. 5 and showing the positional relationship of the electrodes, housing and frame.
Figure 7:
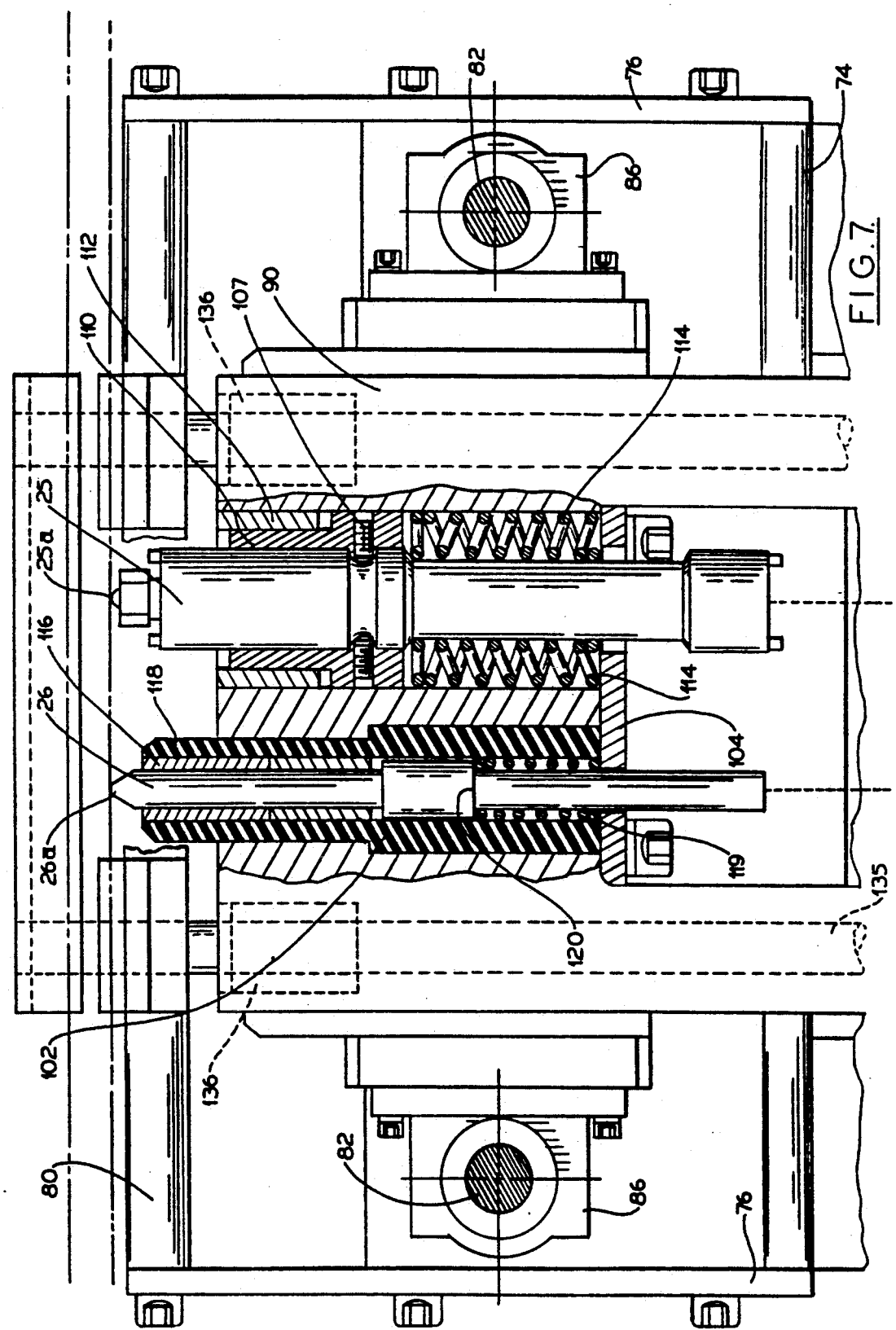
FIG. 7 is an enlarged sectional view of the electrodes supported in the housing.

As shown in FIG. 1, the apparatus 10 generally includes a rod segregation table, indicated generally at 12, having an upper rod transport side 14 (FIG. 5), and defining a rod entry side 16 and rod discharge side 18. The table 12 includes rod movement means in the form of a walking beam assembly indicated generally at 20, for individually moving rods R transversely in spaced relation across the rod segregation table 12 from the rod entry side 16, to an intermediate rod test position indicated generally at 22, and to the rod discharge side 18. Thermoelectric test means, generally indicated at 24, is positioned at the rod test position 22 and includes at least two spaced electrodes 25 and 26 maintained at different temperatures and being adapted and arranged to engage a fuel rod R as it is moved across the table 12 into the rod test position 22 (FIG. 5 and 6). The thermoelectric test means generates a signal representative of the thermoelectrically induced voltage in the rod between the electrodes. Control means, in the form of microprocessing means such as a microcomputer 27 (FIG. 2), is connected to the thermoelectric test means 24 and compares the signal representative of the induced thermoelectric voltage to a predetermined value. When the signal representative of the thermoelectrically induced voltage is different from the predetermined value, a rod offset drive signal is generated to a rod offset drive means 28 positioned on the rod segregation table 12. Rod offset drive means 28 advances longitudinally the tested rod to an offset position on the rod segregation table 12.

Figure 2:
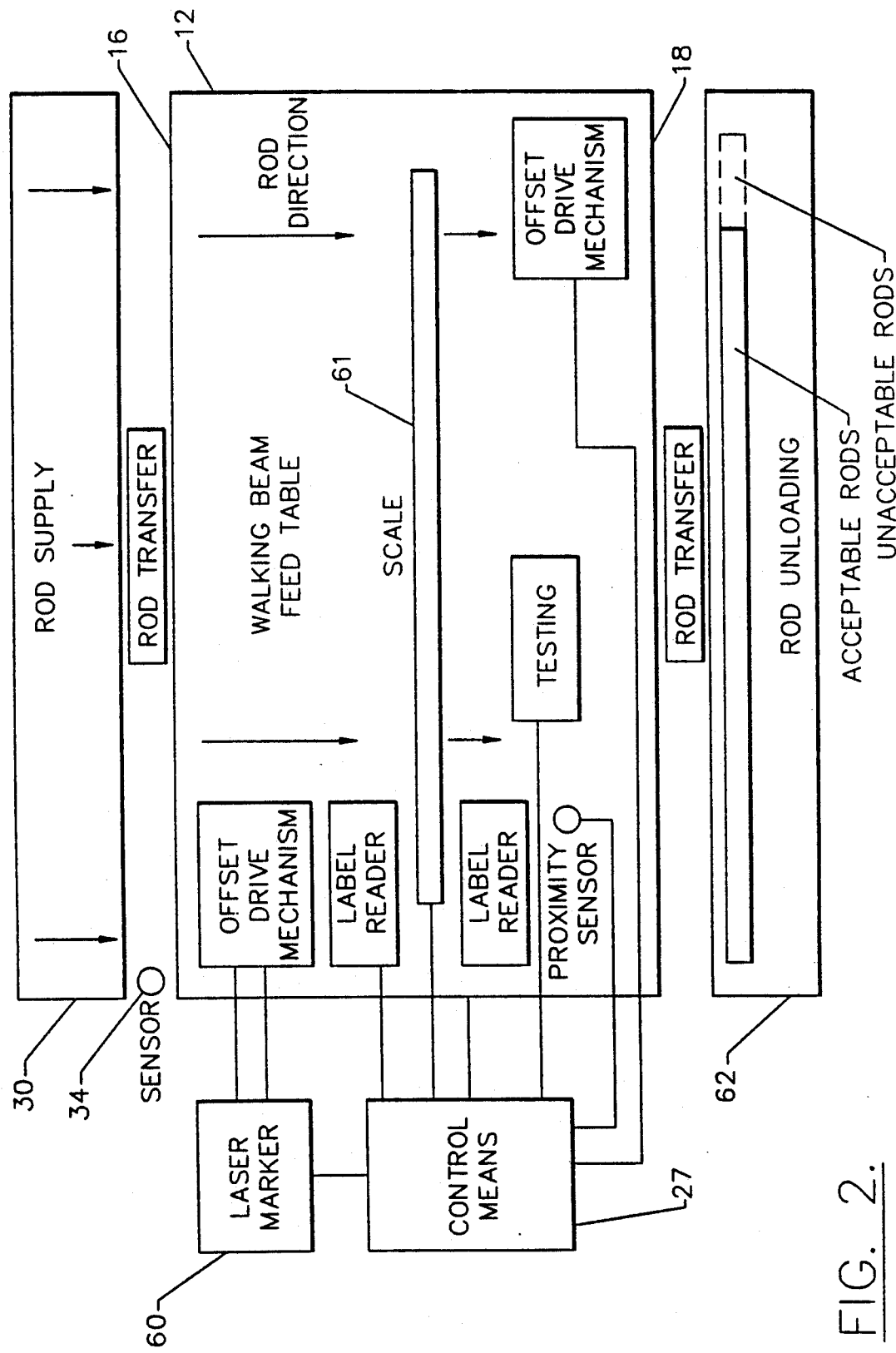
FIG. 2 is a schematic representation of the rod segregation table and showing various components of the system.

As shown in FIGS. 1 and 2, nuclear fuel rods R are stored before processing in side-by-side relationship on a rod supply table 30 adjacent the rod segregation table 12. Each fuel rod R typically is approximately twelve feet long and 0.375 to 0.5 inches in diameter. The rod adjacent the rod entry side 16 of the rod segregation table 12 is transferred onto the rod segregation table 12 by a conventional rod transfer assembly, such as pivoting lift members which pivot in a downwardly extending direction to allow the rod to roll downwardly onto a first rod position on the rod segregation table. A sensor 34 positioned adjacent the rod supply table 30 senses when a rod is positioned on the rod supply table 30 and transmits a signal to the microcomputer 27 which, in turn, activates the rod transfer assembly to move a rod R onto the rod segregation table 12.

As illustrated in FIGS. 1 and 5, the rod segregation table 12 is of conventional construction and includes a substantially rectangular frame 36 having a length longer than the length of each nuclear fuel rod. The frame includes substantially parallel, supports 38 (FIG. 5) extending laterally across the width of the frame. Laterally extending fuel rod support brace assemblies 40 are fixed to respective supports 38 and aligned in substantial parallel relationship with each other. The top portion of each fuel rod support brace assembly 40 includes a top pad surface formed of a soft material such as nylon, and having twelve V-notch grooves 42 aligned with the respective grooves of other support braces. The aligned V-notch grooves form twelve rod support positions 44a–44l on the rod segregation table 12. Each position 44a–44l can support a fuel rod R thereon, and as illustrated in FIG. 1, a total of twelve rods can be supported on the rod segregation table 12. A conventional walking beam assembly 20 moves each rod to a succeeding, adjacent rod support position. As shown in FIG. 5, the rod walking beam assembly 20 includes a support structure assembly 46 secured to each support 38. At least one air cylinder 48 is supported on each support structure 46. Each air cylinder 48 has an output shaft 50 with a top enlarged member. An inverted U-channel 52 is slidably mounted to the air cylinder 48 and support structure 46. Each U-shaped channel member 52 interconnects adjacent U-shaped channel members by brace members (not shown). A rod support bar 54 is fixed to the top portion of each inverted U-channel 52 and includes V-shaped notches 56 for engaging a fuel rod (FIGS. 1 and 5). The rod support bar 54 is dimensioned so that when the air cylinder output shaft 50 is in its most lowered, extended position, the V-shaped notches are positioned below the position of the grooves 42 of the support braces 40 (FIG. 5).

Walking beam drive means in the form of a walking beam air cylinder 58 (FIG. 1) connects to one of the brace members U-shaped channel members 52. As is conventional with walking beam assemblies 20 used in the nuclear industry, the cylinder 58 provides a driving force against all interconnected inverted U-shaped channel members 52 to move the channel members laterally in a back-and-forth movement transverse to the longitudinal direction of the rod segregation table 12. As the U-shaped channels 52 are moved forward in the direction of rod movement, the output shafts 50 of each air cylinder 48 fixed on the cylinder support structures 46 are extended to raise the U-shaped channel members 52 and rod support bars 54 engaging the fuel rod upward. As the fuel rod is raised, the walking beam air cylinder 58 moves forward the U-shaped channel members 52 a predetermined distance and positions each rod over the next succeeding and adjacent rod position. The air cylinder output shaft 50 is lowered and the fuel rod R is lowered into the next, succeeding rod support position. The walking beam air cylinder 58 retracts and draws the U-shaped guide channel back to its original position. This process is repeated to move a fuel rod R from a rod entry position laterally across the rod segregation table 12 to the rod discharge side 18. The microcomputer 27 controls all described movement in a manner for assuring proper movement of a fuel rod across the rod segregation table 12 and in proper timing for allowing testing and other operations as will be described herein.

Figure 3:
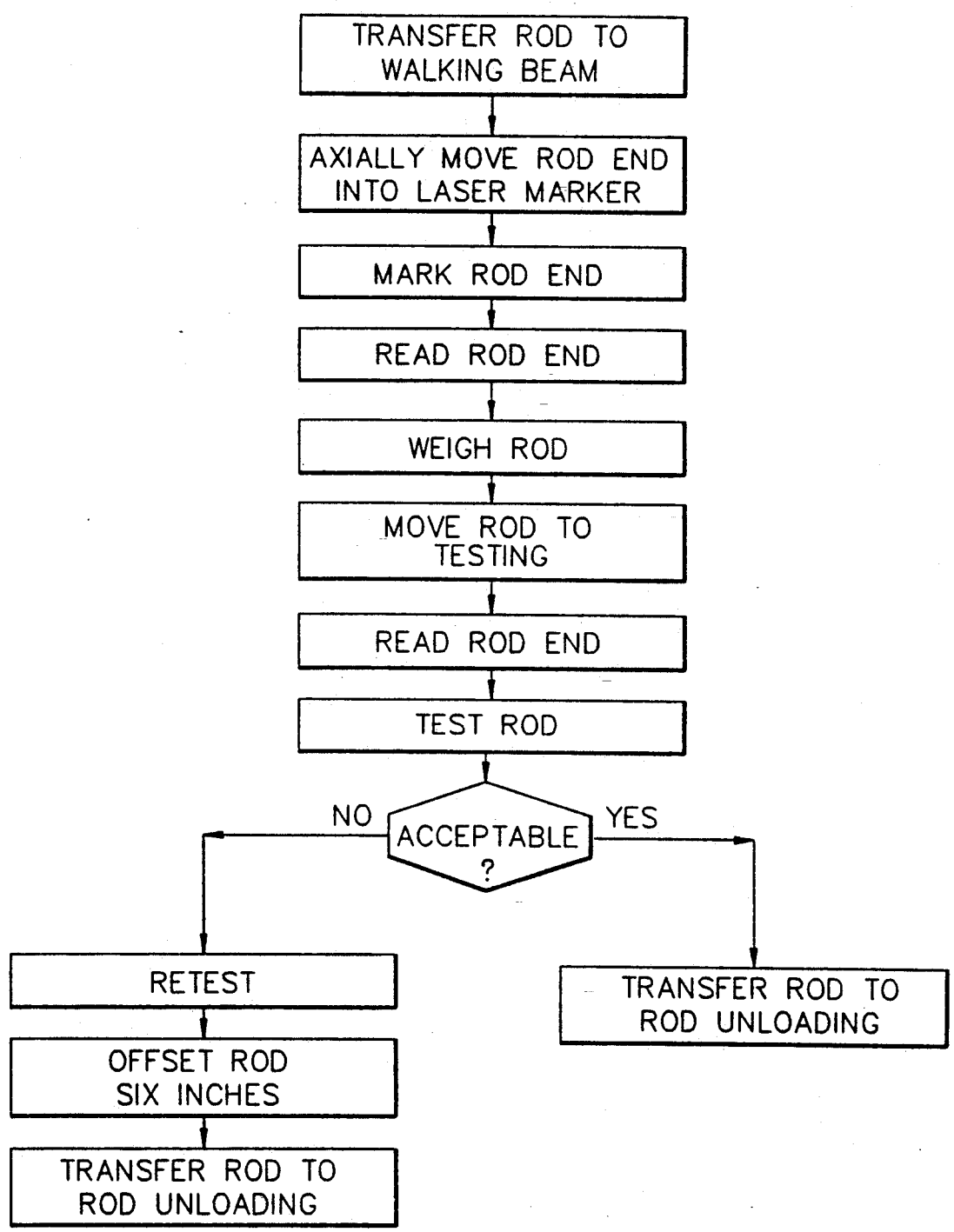
FIG. 3 is a flow chart showing various operations performed on a fuel rod during movement across the rod segregation table.

As shown in FIG. 2 and in the flow chart of FIG. 3, a fuel rod is processed through several operating steps during its movement across the rod segregation table 12. A fuel rod first is transferred to the walking beam 20 as described before. When the rod has reached the third rod support position 44c, it is moved axially by offset drive rolls into a laser marker 60 where an identifying bar code label L is etched onto the end portion of the fuel rod. During laser etching, the fuel rod is rotated. Each fuel rod is given a specific identifying bar code label (FIG. 6). At the seventh rod position 44g, the bar code label is read by a bar code reader for positive identification of the fuel rod R. The fuel rod then is weighed by conventional weigh scales 61 and moved into the eleventh rod test position 44k.

At the eleventh rod test position 44k, the bar code label L is read again for positive identifying identification. The fuel rod R then is thermoelectrically tested. If the rod alloy is unacceptable or determined to be different from a predetermined standard, e.g. a zircaloy fuel rod is tested instead of a desired zirlo fuel rod, the fuel rod is advanced longitudinally six inches to offset the fuel rod from other fuel rods (FIGS. 1-3). The fuel rod then is transferred to the rod unloading table 62 by conventional transfer means. An operator can inspect visually the rod unloading table 62 and determine that the offset fuel rod should be removed from the other fuel rods positioned on the table 62.

Figure 4:
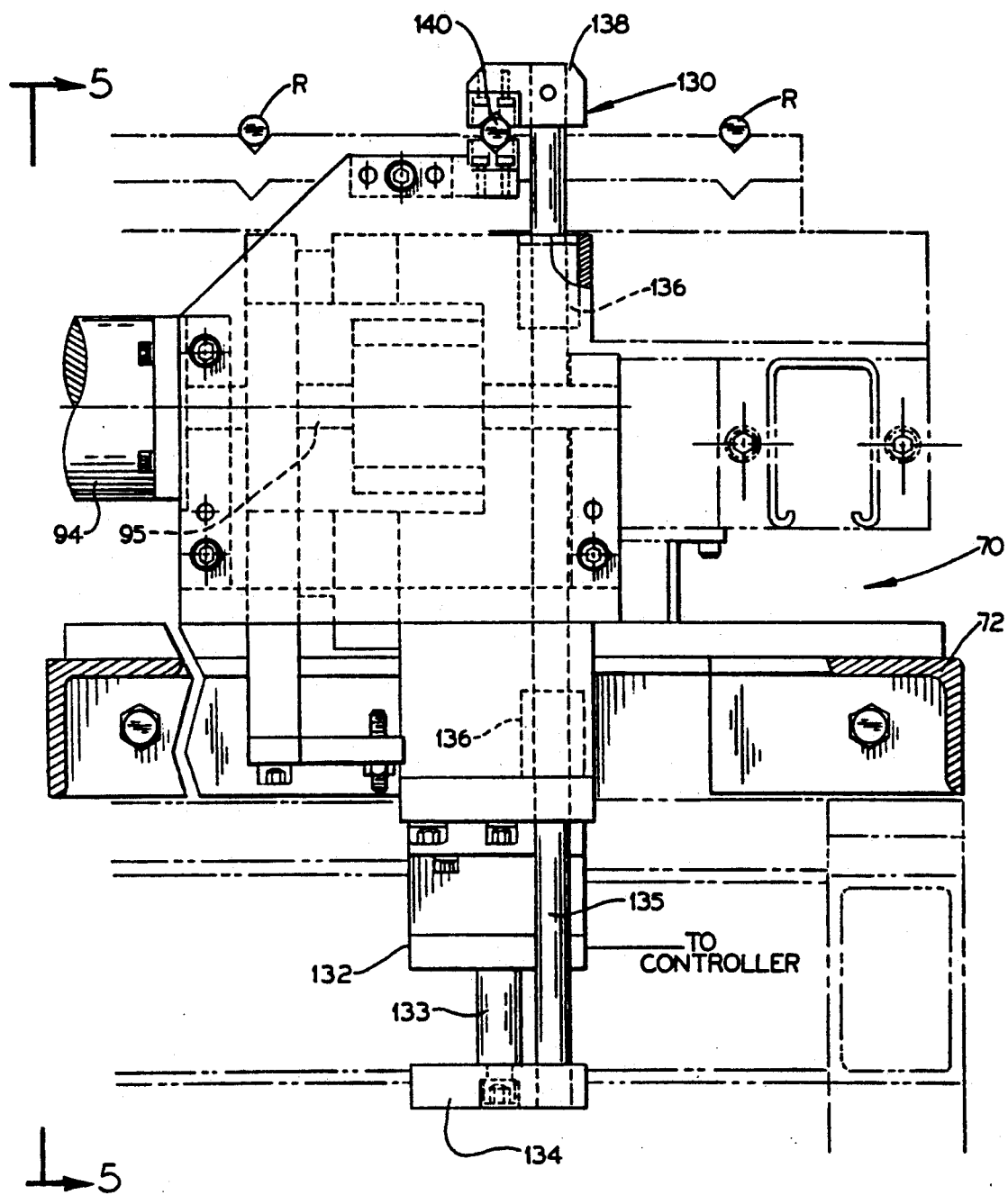
FIG. 4 is a partial side elevational view of the thermoelectric test housing and showing by hidden lines some of the related component parts.

Referring now more particularly to FIGS. 4 through 6, details of the thermoelectric test means 24 are shown. The thermoelectric test means 24 uses the principle of thermoelectric testing, otherwise commonly referred to as the Seebeck effect. Thermoelectric testing is efficient and applicable to the testing of cylindrical rods and objects such nuclear fuel rods. Varying diameters of the rods make little difference in the testing procedure. Reference is made herein to Stuart, C. M., Thermo Electric Differences Used For Metal Sorting, Journal of Testing and Evaluation, JTEVA, Vol. 15, No. 4, July 1987, pp. 224-230. As described therein, thermoelectric testing involves the use of at least two electrodes of known composition and of different temperature exerted against the metal to be tested. The junction between the metal and an electrode forms a thermocouple at each junction. Each junction produces an electromagnetic force (EMF) proportional to the heat applied at each junction, i.e., the temperature of the electrodes. When the temperature is different between the electrodes, a differential voltage is produced at the terminals. The developed voltage is unique to the metals comprising the junctions. By knowing the composition of the electrodes and the temperature of the junctions, it is possible to determine the composition of the tested metal.

There are a variety of different commercially available thermoelectric testing devices which include at least two electrodes maintained at different temperatures and which can be adapted to be arranged to engage a rod positioned in the rod testing position. During testing, signals representative of the thermoelectrically induced voltage in the rod are generated. One particular commercially available model acceptable for use in the present invention is the model 85232WT Alloy Separator manufactured by Technicorp of Rockledge, Fla. In the present invention, the microcomputer 27 connects to a thermoelectric test means device as described above and receives the signal representative of the thermoelectrically induced voltage in the rod and compares the signal of the induced thermo electric voltage to a predetermined value. The predetermined value will be indicative of the signal produced when testing a desired alloy, i.e. in the described example, zirlo. Tested zircaloy rods will produce a voltage signal different from the predetermined value of zirlo. The predetermined value can be found by testing a known zirlo fuel rod.

Referring now to FIGS. 4 through 6, there is disclosed an electrode support fixture, indicated generally at 70, supported by the rod segregation table 12 and which supports the electrodes 25, 26 for engagement with a fuel rod R positioned in the rod test position. The support fixture 70 includes a frame 72 fixed to the table beneath the upper rod transport side 14. The frame 72 is fixed to and extends between the supports 38 defining the rod test position 22 (FIG. 5). The frame has a lower horizontal cross bar member 74, two substantially parallel and vertically extending side plate walls 76, two divided partial front plate walls 77, a rear plate wall 78 and a top brace member 80 (FIG. 5). Two substantially parallel and spaced, cylindrically configured guide bars 82 are fixed to the frame 72 and extend between the rear plate wall 78 and the respective partial front plate walls 77 adjacent respective side plate walls 76 (FIG. 6). The guide bars 82 extend substantially parallel with the supports 38.

A housing indicated generally at 84, is slidably mounted on the guide bars 82 by bearing and collet assemblies 86. The housing 84 includes a U-shaped main housing plate member 88 slidably received on the guide bar 82 by the bearing and collets 86 (FIG. 6). A vertical dove tail slide 89 is bolted thereto. A main electrode support housing body 90 having a dove tail attached member 92 is slidably received onto the dove tail slide 89 and fixed into position. Housing movement drive means in the form of an air cylinder 94 is fixed to the frame 72 and includes an output shaft 95 interconnecting the housing plate member 88. The air cylinder output shaft movement is controlled by the microcomputer 27 connected to the air cylinder 94. The microcomputer 27 signals the air cylinder 94 to move the output shaft in and out and move the housing 84 on the guide bars 82. Bolts 96 extend through both the rear and front plate walls 77, 78 are adjustable for limiting the range of movement of the housing 84 relative to the fixed frame 72.

Two spaced electrode bores 100, 102 extend vertically into the top portion of the electrode support housing body 90. The bores are spaced approximately four inches apart and include generally an electrode retainer plate 104 to aid in retaining electrodes therein. The electrodes 25, 26 are operatively connected to a control which can be a microcomputer for analyzing the voltage signals generated during testing or if a more conventional apparatus such as some commercially available alloy separators. A first electrode 25, referred to as the test electrode is heated to 300° F. The second electrode 26, referred to as the ground electrode remains at ambient temperature, typically about 72° F. in a nuclear fuel manufacturing plant.

As illustrated in FIG. 5, the first bore 100 is somewhat larger than the second bore 102 to accommodate different sized electrodes. The first bore 100 includes the electrode to be heated to 300° F., also known as the test electrode. As illustrated, the test electrode 25, includes a circumferential groove 106 along the upper periphery thereof. A pin 107 fixes into the groove and affixes the electrode to a sleeve bearing 110. The sleeve bearing 110 fits into the upper portion of the bore and includes a liner bushing 112 to aid in insulating the housing body 90 from the heated test electrode. A spring 114 is positioned between the sleeve bearing 110 and the lower retainer plate 104 to exert a continual, upwardly biased force onto the electrode 25. The upward biasing force aids in forcing the test electrode 25 into engagement with a fuel rod positioned in the rod testing position 22.

The second electrode 26, commonly referred to as the ground electrode, is positioned in the second bore 102. A sleeve bearing 116 and insulator 118 surround the ground electrode 26 and insulate the electrode from the housing body 90. A second spring 119 is positioned between a flange 120 on the ground electrode 26 and the lower retainer plate 104 for exerting an upwardly biased force against the electrode.

As illustrated, both the test and ground electrodes 25, 26 include respective tips 25a, 26a for engaging a fuel rod when positioned in the rod testing position 22. The tips provide and maintain more positive contact of electrodes on the fuel rod to be tested. Additionally, a greater portion of the test electrode 25 extends beyond the housing to facilitate cooling thereof when testing is completed.

As illustrated in FIGS. 4 and 5, a rod engaging clamp means, indicated generally at 130, is carried by the housing s4 and is vertically moveable between 1) a lowered position where the rod engaging clamp means 130 is positioned beneath the upper rod transport side 14 of the rod segregation table 12, 2) a raised position above the level of the upper rod transport side 14 and of a rod positioned in the rod test position 22, and 3) an intermediate position where the rod engaging clamp means 130 is engaged with the upper surface of a rod positioned in the rod test position. The rod engaging clamp means 130 engages the upper surface of the rod and exerts pressure thereagainst to ensure contact of the test and ground electrodes 25, 26 with the fuel rod.

The rod engaging clamp means 130 includes an air cylinder 132 (FIG. 4) mounted to the housing 22 and it is operatively connected to the microcomputer 27. The air cylinder 132 has a downwardly extending output shaft 133. The air cylinder output shaft movement is controlled by the microcomputer 27. A cross member 134 is mounted on the air cylinder output shaft 133 and two substantially parallel, spaced and vertically extending shafts 135 extend through the main electrode support housing body 90 and upward beyond the housing body. Ball bushings 136 are fixed in the housing body 90 and receive the upwardly extending shafts 135 therethrough to facilitate guidance. An elongate rod clamp member 138 is fixed by pins to the upper ends of the shaft 135 and extends therebetween. The elongate rod clamp member 138 includes a lower rod engaging surface having groove 140 for engaging the upper surface of the fuel rod positioned in the rod testing position (FIG. 4).

When the output shaft 133 of the air cylinder 132 is vertically and downwardly extended, the Vertically extending shafts 135 are lowered. The shafts 135 are dimensioned so that when the air cylinder output shaft 133 is extended, the rod clamp member 138 is positioned below a rod positioned in the rod test position and below the upper rod transport side 14 of the rod segregation table. When the output shaft 133 is fully retracted the elongate rod clamp member 138 is positioned above the level of a rod R positioned in the rod test position 22. Movement of the rod engaging clamp means 130 between lowered and raised positions facilitates movement of a rod from an adjacent rod position into the rod test position. When the output shaft is fully extended, the elongate rod clamp member 138 is positioned below the level of a rod and the rods are free to move along the rod segregation table 12 without interference from the elongate rod clamp member 138.

As shown in FIG. 1, rod offset drive means is positioned at rod position eleven corresponding to the rod test position 22 of a rod R to be tested. The rod offset drive means 28 advances a rod longitudinally to an offset position on the rod segregation table 12 after receiving an offset drive signal from the microcomputer 27. The rod offset drive signal is generated when the voltage signal representative of the induced thermoelectric voltage is different from the predetermined value. For example, a preferred zirlo fuel rod is tested, and the predetermined value corresponds to the results achieved when testing the zirlo fuel rod. The results obtained when testing a zircaloy fuel rod then are compared with the predetermined value corresponding to the testing of a zirlo fuel rod. If there is a difference, the offset drive signal is generated and transmitted to the rod offset drive means 28.

As illustrated, the rod offset drive means 28 includes two pivoting rollers 152 positioned on the rod segregation table 12 at the rod test position 22. Roller drive means in the form of an actuator or other conventional drive mechanism pivots the rollers 152 into engagement with the rod R after a rod offset drive signal has been generated. The rollers 152 advance the rod to an offset position on the rod segregation table.

After a rod has been tested, it is transferred to the rod unloading table 62. A rod transfer assembly (not shown in detail) is positioned adjacent the rod segregation table 12 for transferring rods from the table onto the rod unloading table. Various conventional rod transfer systems; may be used, including the pivoting arms as noted above.

METHOD OF OPERATION

During operation, rods are transferred from the rod supply table 30 onto the rod segregation table 12. As one rod is moved from the first rod position 44a into the second rod position 44b, another rod from the rod supply table is transferred into the first rod position. As the rods move laterally across the rod segregation table 12, other rods are transferred from the rod supply table onto the rod segregation table. When a rod has reached the third rod position 44c, it is advanced by drive rollers 28a (FIG. 1) similar to those positioned at the rod test position into the laser 60 (FIG. 2) where the bar code label is burned thereon. The rod is retracted from the laser and moved into succeeding rod positions. In the seventh rod position a bar code reader positioned above the rod segregation table reads the bar code to positively identify the fuel rod and store the identifying information in the microcomputer. The fuel rod then is weighed and the weight entered into the microcomputer memory. The rod is moved into succeeding rod positions, and then into the eleventh rod test position 22. During movement of the fuel rod from the tenth into the eleventh rod test position 22, the rod engaging clamp means 130 has been moved into a lower position where the rod engaging clamp means 130 is positioned beneath the upper rod transport side of the rod segregation table. In this position, the rod engaging clamp means 130 will not interfere with, movement of the rod. Additionally, the housing 84 is moved on the guide rails to a laterally offset nontesting position.

After a fuel rod is positioned in the rod test position, the rod engaging clamp means 130 is raised to its fullest extent and the housing 84 moved into the rod testing position. The rod engaging clamp means 130 then is lowered against the upper surface of the rod positioned in the rod test position to exert pressure of the rod R against the electrode tips. The microcomputer 27 activates the thermoelectric test means and the test electrode is heated to 300° F. For a standard test procedure, the ground electrode can be heated to a lower 70°-80° F. for consistent results. Heated contact is made for ten seconds and during that time a voltage is generated at each junction of the test and ground electrodes. A voltage circuit is established and a voltage signal representative of the thermoelectrically induced voltage in the rod between the electrodes is generated. The microcomputer 27 includes means for receiving the signal and comparing the signal representative of the induced thermoelectric voltage to a predetermined value corresponding to the zirlo fuel rod. If the value derived from testing a fuel rod is different from the predetermined value, the test preferably is repeated again. By repeating the test again, verification and one hundred percent reliability, desirably is obtained. If during the second test, the value is determined different, the microcomputer 27 generates an offset drive signal to the offset drive means 150 for advancing the unacceptable fuel rod six inches. The rod is moved into the twelfth rod position and then transferred onto the rod unloading table 62. At this time, an operator visually inspects the rods for any offset rods to determine which rods must be removed from the rod lot.

In the drawings and specification, there has been set forth a preferred embodiment of the invention, and while specific terms are employed, they are used in a generic and descriptive sense only and not for purposes of limitation.

We claim:

1. An apparatus for segregating elongate cylindrical rods of undesirable alloy composition from rods having a desired alloy composition comprising, a rod segregation table having an upper rod transport side and defining a rod entry side and rod discharge side, and including rod movement means for individually moving rods transversely in substantially parallel spaced relation across said upper rod transport side of said rod segregation table from said rod entry side, to an intermediate rod test position, and to said rod discharge side, thermoelectric test means positioned at said rod test position, said thermoelectric test means having at least two spaced electrodes maintained at different temperatures and being adapted and arranged to engage a cylindrical rod to be tested as it is moved into said rod test position so as to induce a thermoelectric voltage at junctures of the rod and two spaced electrodes, and means connected to said electrodes for receiving signals representative of said induced thermoelectric voltage and for comparing said signals to a predetermined value, and means for moving the rod to an offset position on the rod segregation table when said signals differ from the predetermined value by a predetermined amount.

2. The apparatus as claimed in claim 1 wherein said means connected to said thermoelectric test means for comparing said signals representative of thermoelectric voltage includes microprocessing means.

3. The apparatus as claimed in claim 1 including means for generating an offset drive signal when said signal representative of said induced thermoelectric voltage is different from said predetermined value, and wherein said movement means includes rod offset drive means positioned on said rod segregation table at said rod test position and connected to said offset drive signal generating means for receiving said offset drive signal, and for advancing a rod longitudinally to said offset position on said rod segregation table from the longitudinal position of other rods moved along said rod segregation table after receiving an offset drive signal.

4. The apparatus claimed in claim 3 wherein said rod offset drive means includes pivotable roller means positioned on said table at said rod test position and roller drive means for pivoting said roller means into engagement with said rod and for advancing a rod longitudinally into said offset position on said rod segregation table.

5. The apparatus as claimed in claim 1 wherein said rod testing table includes longitudinally spaced apart ends and laterally spaced apart opposite sides.

6. The apparatus as claimed in claim 1 including means biasing the electrodes into engagement with a rod positioned in the rod testing position.

7. The apparatus as claimed in claim 1 wherein said thermoelectric test means includes an electrode support fixture supported by said table, said electrode support fixture comprising, (a) a housing positioned under said upper rod transport side of said rod segregation table, and (b) means fixed to said table and supporting said housing for movement of said housing from a first rod test position to a second, laterally offset nontesting position, and said spaced electrodes being supported by said housing and being positioned to engage the bottom portion of a rod when said housing is positioned in said rod test position.

8. The apparatus as claimed in claim 7 including rod engaging clamp means carried by said housing and being vertically movable between 1) a lowered position where said rod engaging clamp means is positioned beneath said upper rod transport side of said rod segregation table, 2) a raised position above the level of said upper rod transport side and 3) an intermediate position where the rod engaging clamp means is engaged with the upper surface of a rod positioned in the rod test position.

9. The apparatus as claimed in claim 8 wherein said rod engaging clamp means includes an air cylinder mounted on said housing and having a downwardly extending output shaft, a cross member mounted on said air cylinder output shaft, two substantially parallel, spaced and vertically extending shafts having lower ends mounted to said cross member and having an elongate rod clamp member extending between the upper ends of each shaft and being mounted thereto, said elongate rod clamp member including a lower rod engaging surface for engaging the upper surface of a rod positioned in said rod test position when said rod engaging clamp means is in said intermediate position.

10. The apparatus claimed in claim 8 including an air cylinder operatively connected to said rod engaging clamp means for moving said rod engaging clamp means into said lowered, raised and intermediate positions.

11. The apparatus as claimed in claim 7 wherein said means fixed to said table and supporting said housing for lateral offset movement includes a frame supported by said table, two substantially parallel and spaced guide bars fixed to said frame and extending beneath the upper rod transport side of said rod segregation table, means mounting said housing for slidable movement on said guide bars, and drive means mounted to said frame and interconnected to said housing for moving said housing on said guide bars.

12. A support fixture for supporting at least two spaced electrodes maintained at different temperatures for contacting a cylindrical rod as it is moved into a rod test position on a rod segregation table, said support fixture including
 a frame adapted for interconnection to a rod segregation table in a position beneath the rod test position,
 two substantially parallel and spaced guide bars fixed to said frame,
 a housing slidably mounted on said guide bars,
 drive means mounted to said frame and interconnected to said housing for moving said housing on said guide bars, and
 at least two spaced electrode bores extending into said housing, each bore being dimensioned to carry therein an electrode for engaging and testing a rod positioned in the rod test position.

13. The support fixture as claimed in claim 12 including rod engaging clamp means carried by said housing, said rod engaging clamp means including an air cylinder mounted on said housing and having an output shaft, a cross member mounted on said output shaft, two substantially parallel, spaced shafts having first ends mounted to said cross member, and an elongate rod clamp member extending between the second ends of each shaft and being mounted thereto, said elongate rod clamp member including a rod engaging surface for engaging a rod positioned in said rod testing position.

14. A method of segregating an elongate cylindrical rod of undesirable alloy composition from rods having a desired alloy composition comprising
 moving a plurality of rods in side-by-side relationship transversely along a predetermined path of travel on a rod segregation table,
 thermoelectrically testing each rod in sequence, and comparing a signal representative of the induced thermoelectric voltage to a predetermined value, and
 advancing a rod longitudinally to an offset position if the signal representative of the induced thermoelectric voltage is determined to be different from the predetermined value.

15. The method according to claim 14 including the step of advancing the rod into a laser for burning an identifying bar code label on each rod end before each rod is thermoelectrically tested.

16. The method according to claim 14 including the step of thermoelectrically testing the rod a second time before advancing the rod longitudinally to said offset position when the signal representative of the induced thermoelectric voltage is determined to be different from the predetermined value.

* * * * *